(12) United States Patent
Matern et al.

(10) Patent No.: US 6,428,530 B1
(45) Date of Patent: Aug. 6, 2002

(54) GRIP OF ENDOSCOPIC INSTRUMENT

(75) Inventors: Ulrich Matern, Bollschweil; Peter Waller, Gauting, both of (DE)

(73) Assignee: Klinikum der Albert-Ludwigs-Universitat (DE)

( * ) Notice: Subject to any disclaimer, the term of this patent is extended or adjusted under 35 U.S.C. 154(b) by 0 days.

(21) Appl. No.: 09/355,588

(22) PCT Filed: Dec. 23, 1997

(86) PCT No.: PCT/DE97/03019
§ 371 (c)(1),
(2), (4) Date: Dec. 1, 1999

(87) PCT Pub. No.: WO98/29024
PCT Pub. Date: Jul. 9, 1998

(30) Foreign Application Priority Data

Jan. 3, 1997 (DE) .......................................... 197 00 114

(51) Int. Cl.[7] .............................................. A61B 17/00
(52) U.S. Cl. ............................ 606/1; 600/131; 606/205
(58) Field of Search ................................ 600/131, 102, 600/104; 606/1, 205, 45

(56) References Cited

U.S. PATENT DOCUMENTS 1,880,551 A * 10/1932 Wappler
1,969,342 A * 8/1934 Wappler ........................ 128/7
4,461,281 A * 7/1984 Carson ........................... 128/3
5,400,768 A * 3/1995 McNamara et al. ........... 128/4
5,910,105 A * 6/1999 Swain et al. ................. 600/131

FOREIGN PATENT DOCUMENTS

DE 4216874 C1 * 7/1993 ............. A61B/1/00
DE 4228909 A1 * 3/1994 ........... A61B/17/12

* cited by examiner

Primary Examiner—Linda C. M. Dvorak
Assistant Examiner—Jocelyn Ram
(74) Attorney, Agent, or Firm—St. Onge Steward Johnston & Reens LLC

(57) ABSTRACT

Described is a grip part of an endoscopic instrument with at least a movable control element for mechanical guidance of a tool unit mounted on the distal end of the shaft of the endoscopic instrument and a main body.

The invention is distinguished in that the main body has a largely symmetrical shape which is ergonomically adapted to the human hand such that the endoscopic instrument can be encircled at least partially by the palm of a hand balled into a fist and that the operating element is movable relative to the main body.

8 Claims, 1 Drawing Sheet

GRIP OF ENDOSCOPIC INSTRUMENT

TECHNICAL FIELD

The invention concerns a grip part of an endoscopic instrument with at least one movable control element for mechanical control of a tool element mounted on the distal shaft end of the endoscopic instrument and a main body.

STATE OF THE ART

The success of the application of endoscopic instruments in surgery depends in no small part upon the operator-friendliness of such instruments, which in very large degree is determined by the ergonomic configuration of the grip parts.

Thus, for example, so-called scissors grips have long been known which through activation permit the opening and closing of forceps mounted on the distal side of endoscopic instruments. In the case of grip parts configured in this manner, if rotational movements at the distal side of the forcep in open or closed position are needed, the operator must turn his wrist in a corresponding manner. However, this is possible only to a certain angle which is predetermined through the maximum rotational motion of the human wrist. Further twisting is possible through the rotation of the shaft with the help of a knurled nut. In addition, branch grips and scissors grips are not fitted to individual hand sizes.

PRESENTATION OF THE INVENTION

The object of the invention is to ergonomically design a grip part of an endoscopic instrument with at least one movable control element for mechanical control of a tool unit mounted on the distal end of the shaft of the endoscopic instrument and a main body such that the grip part is suitable both for left-handed and right-handed use. To the greatest extent possible, the grip part must be designed with simple spatial geometry so that the associated manufacturing costs can be reduced. In addition, individual adjustment actions should be possible on the grip part in order to take into consideration the various hand sizes.

The solution to the object on which the invention is based is indicated in claim 1 Advantageous embodiments of the invention presented in the dependent claims.

According to the invention, a grip part of an endoscopic instrument with at least one movable control element for mechanical guidance of a tool unit mounted on the distal end of the shaft of the endoscopic instrument and a main body is designed such that the main body has a largely symmetrical shape which is ergonomically adapted to the human hand such that the endoscopic instrument can be held fast solely by means of the main body which can be enclosed at least partially by the palm of a hand which is balled to form a fist and that the control element is movable relative to the main body.

The invention is based on the idea of designing the main body of the grip part as symmetrically as possible and in a size such that the main body can be held in the palm of a hand which is balled into a fist. Advantageous shapes of main bodies of this kind are spherical bodies such as a ball or oblong shapes which advantageously correspond to the width of the palm of a hand and can be largely encircled by the palm in curved posture.

As a result of the symmetrical design of the main body according to the invention, it is possible for the operator to grasp the grip part either with the left hand or with the right hand. It can happen, particularly in performing surgical procedures, that the operator must operate several endoscopic instruments at the same time; in this case it is very advantageous if the operator can operate one and the same endoscopic instrument both with the left hand and with the right hand in order to be able to possibly perform the procedures more rapidly and thus with less stress on the patients.

The main body is advantageously mounted in proximal extension to the axis to the instrument and should be attached so as to be slidable with respect to the control element. In this manner it is possible to adjust the grip part individually to the size of the operator's hand.

While it is possible to hold the entire endoscopic instrument with only the palm of the hand, which is able to encircle the main body, it is nevertheless advantageous for a counter hold to be attached to the main body in distal direction with which the operator can apply at least one of his fingers for steadying. The control element advantageously is mounted movably on the counter hold.

BRIEF DESCRIPTION OF THE DRAWINGS

The invention is described below, without limitation of the general inventive idea, using exemplary embodiments with reference to the drawings.

DESCRIPTION OF AN EXEMPLARY EMBODIMENT

Figure 1:
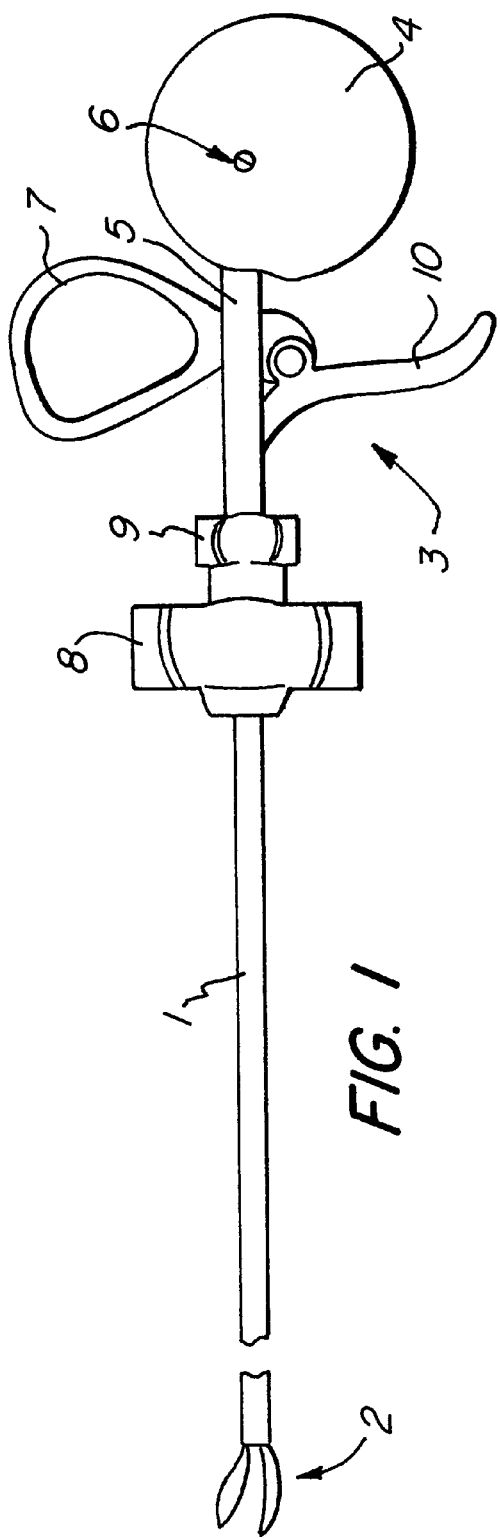
FIG. 1 shows a schematic description of the grip part of an endoscopic instrument.
Figure 3:
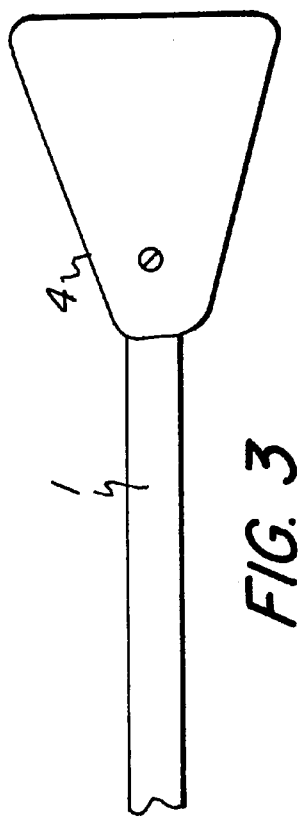
FIG. 3 depicts a conical configuration of the main body.

In FIG. 1, an endoscopic instrument with an instrument shaft axis 1 and a tool unit 2 arranged at the distal side of the shaft 1, the tool unit in the case of the exemplary embodiment being a gripper unit. At the proximal side, a grip part 3 is arranged on the instrument shaft 1 with which it is possible to open and close the pliers-like tool unit and to rotate the instrument shaft axis. According to the invention, grip part 3 has a main body 4 which is configured in the manner of a ball and which can be encircled by the palm of the left hand as well as the right hand of the operator at a minimum such that the entire endoscopic instrument can be carried by main body 4. Main body 4 is mounted on the proximal side on an extension 5 and can be slid relative to extension 5 and can be fastened with a fastening unit 6 which, for example, can be configured in the manner of a stud screw, to the extension 5. As a result of its being slidable, it is possible to adjust main body 4 relative to control element 7 such that it is ergonomically comfortable for an operator to operate grip part 3. To increase the holding power, a holding bar 10 is provided onto which at least one finger can be laid in order to increase the counter pressure of main body 4 in the direction of the palm of the hand of an operator (not depicted in the drawing).

By moving control element 7 relative to main body 4, tool unit 2 can be opened and closed. In addition, knurled screws 8 and 9 project outwards with which rotation of tool unit 2 together with instrument shaft 1 around the shaft axis is possible and secondly, a firm connection of the instrument shaft to grip part 3 can be formed.

Figure 2:
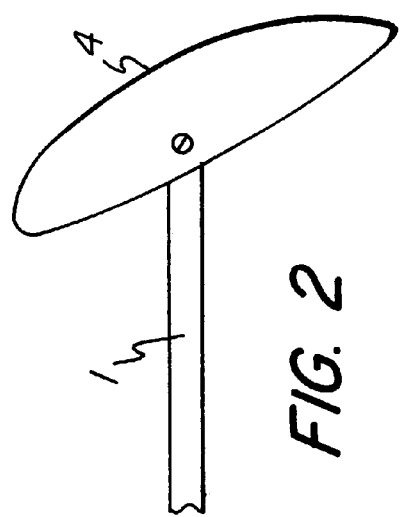
FIG. 2 shows an alternative embodiment for a main body.

In FIG. 2, an alternative embodiment of a main body 4 is indicated which is wedge-shaped in cross section and is ergonomically adapted to the palm of the human hand. With this form as well it is possible to hold the entire endoscopic instrument by only encircling grip part 4.

What is claimed is:

1. A grip for use with a surgical instrument, comprising:
an extension having a distal end and a proximal end, said distal end being connectable to a shaft of a surgical instrument;
a main body having a symmetrical shape and being adjustably attached to said proximal end of said extension;
a rotation device located between and adapted to be in contact with both the shaft and said distal end of the extension, said rotation device for rotating the shaft about its axis;
a finger supporting device fixed to said extension and located between said rotation device and said main body for facilitating actuation of the surgical instrument; and
a control element pivotably attached to said finger supporting device for actuating the surgical instrument.

2. The grip according to claim 1 wherein said main body is generally spherical.

3. The grip according to claim 1 wherein said main body has a wedge-shaped configuration substantially enclosable by the palm of a hand.

4. The grip according to one of claims 1 through 3, wherein a distance between said main body and said control element is fixably adjustable.

5. The grip according to claim 4, wherein said main body is adapted to be fixably mounted to the shaft and slidable.

6. The grip according to claim 1, further comprising a set screw for adjustably fixing said main body to said extension.

7. The grip according to claim 1, wherein said main body is adapted to be adjustable along the axis of the shaft.

8. The grip according to claim 1, wherein said main body is substantially enclosable by either hand of a user.

* * * * *